United States Patent [19]

Uyama

[11] Patent Number: 5,260,981
[45] Date of Patent: Nov. 9, 1993

[54] DEVICE FOR INSPECTING AN ARTICLE

[75] Inventor: Kiichiro Uyama, Tokyo, Japan

[73] Assignee: Kabushiki Kaisha Toshiba, Kawasaki, Japan

[21] Appl. No.: 890,144

[22] Filed: May 29, 1992

[30] Foreign Application Priority Data

May 31, 1991 [JP] Japan .................................. 3-129890

[51] Int. Cl.$^5$ .......................................... G01N 23/04
[52] U.S. Cl. ........................................ 378/57; 378/70; 378/86
[58] Field of Search .................. 378/62, 4, 6, 7, 64, 378/86, 14, 87, 88, 70, 99, 57, 146, 147, 148

[56] References Cited

U.S. PATENT DOCUMENTS

| 4,870,670 | 9/1989 | Geus  | 378/57 |
| 5,022,062 | 6/1991 | Annis | 378/57 |

FOREIGN PATENT DOCUMENTS 0271723 6/1988 European Pat. Off. .

Primary Examiner—Paul M. Dzierzynski
Assistant Examiner—Don Wong
Attorney, Agent, or Firm—Oblon, Spivak, McClelland, Maier & Neustadt

[57] ABSTRACT

A device for inspecting an article, in which a radiation source irradiates a plane-shaped radiation to an article in order to inspect the content of the article without destroying it. Scattered radiation from the article is applied to a radiation detector through a slit which is formed coincident with a line passing through a focus of the radiation source and which continuously passes a constant full field of scattered radiation. The radiation detector is disposed in parallel with the slit and scattered radiation detected by the radiation detector is displayed as an image of the region of the article which was irradiated by the plane-shaped radiation.

8 Claims, 5 Drawing Sheets

DEVICE FOR INSPECTING AN ARTICLE

BACKGROUND OF THE INVENTION

This invention relates to an article inspection device including separate detectors for primary and scattered radiation.

An example of the prior art is disclosed in U.S. Pat. No. 4,870,670, and is illustrated in FIG. 7.

As shown in FIG. 7, a fan-shaped X-ray beam 1 which is generated by X-radiator 2 and a collimator 3 is irradiated onto an article 4 which is conveyed by conveyor belt 5 in the direction of the arrow X. As a result of that, scattered X-ray beams are emitted by the article 4 in all directions.

A scintillator 6 receives a part of the emitted scattered X-ray beams through diaphragms 7 of a modulator 8 and generates visible rays. The visible rays generated from the scintillator 6 are converted into electrical signals by an opto-electrical transducer 9, so that the scattered X-ray beams are detected.

The detected scattered X-ray beams as an output from the opto-electrical transducer 9 are input into an image processor 10, and then the image of the region of the article 4 is generated.

The image is visually displayed on a TV monitor 11. The primary X-ray beams are detected by X-ray line sensor 12 and are displayed as a primary X-ray beam image by the TV monitor 11 through a multiplexer 13 and the image processor 10.

However, in this prior art, the efficiency of detecting the scattered radiation is remarkably low because the diaphragms of the modulator are small. Thus, noise occurs in the picture of the TV monitor.

SUMMARY OF THE INVENTION

It is an object of the invention to provide a device for inspecting an article providing good efficiency of detecting scattered radiation and high quality of pictures.

A specific construction in order to achieve this object is equipped with: radiation generating means for converting a radiation generated from a radiator into a plane-shaped radiation and irradiating the plane-shaped radiation to an article; pass means having a slit which is located to be coincident with a line passed through the radiator for passing a scattered radiation emitted from the article as a result of being irradiated by the plane-shaped radiation; and radiation detect means having a spatial resolution and a detecting face disposed in parallel with the slit formed the pass means for detecting the scattered radiation which passed through the pass means.

With a device for inspecting an article of this invention constructed as above, the plane-shaped radiation which is generated from the radiator is irradiated to the article; the scattered radiation emitted from the article passes through the slit formed in the pass means and is formed an image on the detecting face in parallel each other so that the detecting face is disposed in parallel with the slit formed the pass means; each slice of the image is detected by the radiation detect means at the same time; and the detected image is integrated in accordance with the direction of the line of the image.

DETAILED DESCRIPTION OF THE PREFERRED EMBODIMENT

The invention is described in detail below with reference to various embodiments.

A first embodiment of this invention applied to an article inspection device used X-ray beam will be described with reference to FIGS. 1 through 4.

The overall layout will be described with reference to FIGS. 1 and 2.

Figure 1:
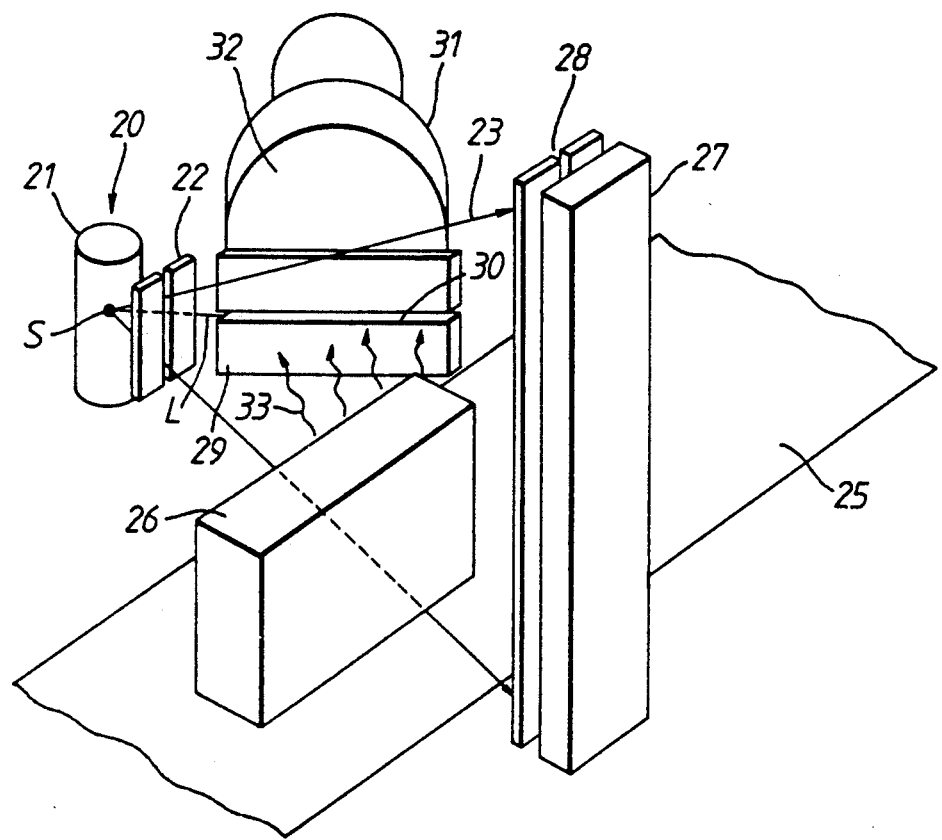
FIG. 1 is a perspective view showing a first embodiment of the present invention.
Figure 2:
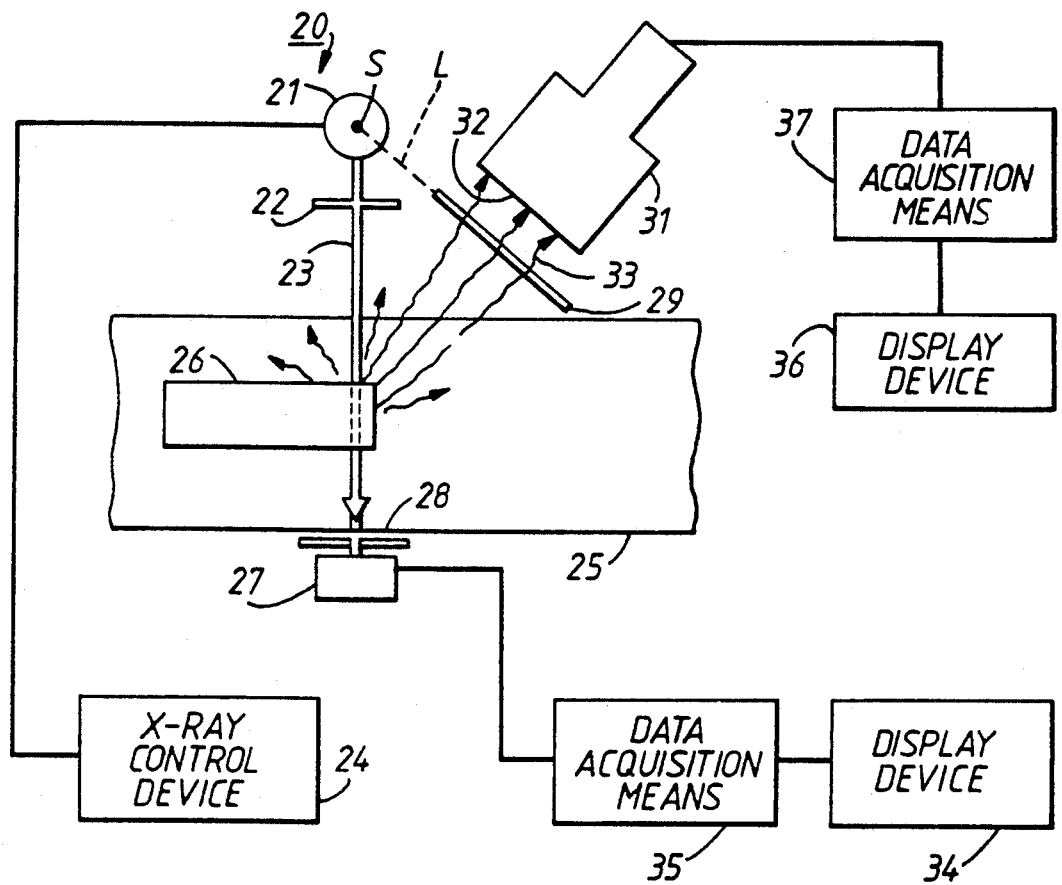
FIG. 2 is a detailed view showing a first embodiment of the present invention.

As shown FIGS. 1 and 2, an X-ray beam generate means 20 consists of an X-ray tube 21 as a radiation source having an X-ray beam focus S and a slit 22 disposed in front of the X-ray tube 21 to convert X-rays generated from the X-ray tube 21 into a fan-shaped X-ray beam 23 of about 1 mm in thickness. The X-ray tube 21 is controlled by an X-ray control device 24.

The X-ray beam generate means 20 is disposed to one side of a conveyor belt 25 which conveys an article 26 as a subject. So the article 26 is conveyed across the fan-shaped X-ray beam 23 generated from the X-ray tube 21 by the conveyor belt 25.

An X-ray beam line detector 27 having about four hundred individual detectors is disposed on another side of the conveyor belt 25 opposite to the X-ray beam generate means 20 and detects a primary X-ray beam which is transmitted through the article 26. A primary X-ray beam slit 28 is disposed on an incident side of the X-ray beam line detector 27, causes the primary X-ray beam to pass through and rejects a scattered X-ray beams.

A scattered X-ray beam pass means 29 having a slit 30 which is formed in accordance with a line L passing through the X-ray beam focus S of the X-ray tube 21 as shown in FIG. 1.

An X-ray television 31 used as a scattered X-ray beam detector having about four hundred channels comprises an X-ray beam detecting face 32 to be disposed in parallel with the scattered X-ray beam pass means 29. Scattered X-ray beams 33 emitted by the article 26 as a result of being irradiated by the fan-shaped X-ray beam 23 pass through the slit 30 and are detected by the X-ray television 31.

The X-ray beam line detector 27 is connected to a display device 34 through a data acquisition means 35 and the X-ray television 31 is connected to a display device 36 through a data acquisition means 37.

The operation of this embodiment will now be described.

The fan-shaped X-ray beam 23 generated by the X-ray beam generate means 20 is detected by the X-ray beam line detector 27 through the primary X-ray beam slit 28. As the fan-shaped X-ray beam 23 is irradiated to the article 26 which is conveyed by the conveyor belt 25 at a speed of 15 meters a minute, the article 26 is transmitted by the fan-shaped X-ray beam 23 and a part of the fan-shaped X-ray beam 23 is scattered by the article 26, and the scattered X-ray beam is emitted in every direction. The scattered X-ray beam 33 which passes through the slit 30 is detected by the X-ray television 31.

While the article 26 is conveyed by the conveyor belt 25, the changing primary X-ray beam and scattered X-ray beam are detected by the X-ray beam line detector 27 and the X-ray television 31 respectively. And then during the time the conveyor belt 25 moves a two millimeter distance (an eight-millisecond period) the detected primary X-ray beam and scattered X-ray beam are respectively integrated. The integrated data is hereinafter referred to as "1 line data".

Output of the four hundred individual detectors forming the X-ray beam line detector 27 is integrated, converted from an analog signal into a digital signal, and corrected by the data acquisition means 35. This correction consists of offset correction and gain correction. The offset correction is the output value of the individual detector minus an output value of the individual detector in case of the primary X-ray beam didn't strike against the article 26. The gain compensation is the value after the offset compensation in the case that the article 26 is irradiated by the primary X-ray beam divided by a value after the offset correction in the case that the line detector 27 is directly irradiated by the primary X-ray beam.

After correcting, the output of the data acquisition means 35 as "1 line data" is memorized by a memory (not shown) of the display device 34. At this time the "1 line data" is memorized in the memory being appropriate to a vertical line of the left side of a screen (not shown) of the display device 34. The vertical line of the screen indicates the direction of forming the individual detectors of the X-ray beam line detector 27.

For the next eight-millisecond period "1 line data" is detected in the same way as described above, the next "1 line data" is memorized in the direction to the right side of the previous "1 line data" in the memory and so forth.

Accordingly, if the conveyor belt 25 moves in one meter in distance, five hundred sets of "1 line data" are measured.

The five hundreds line data sets indicate a primary X-ray beam image being suitable for the article 26. The primary X-ray beam image is displayed on the screen of the display device 34 in accordance with the five hundred line data obtained from the data acquisition means 35.

The operation of detecting 1 line data by the X-ray television 31 will now be described with reference to FIG. 3 and FIG. 4.

Figure 3:
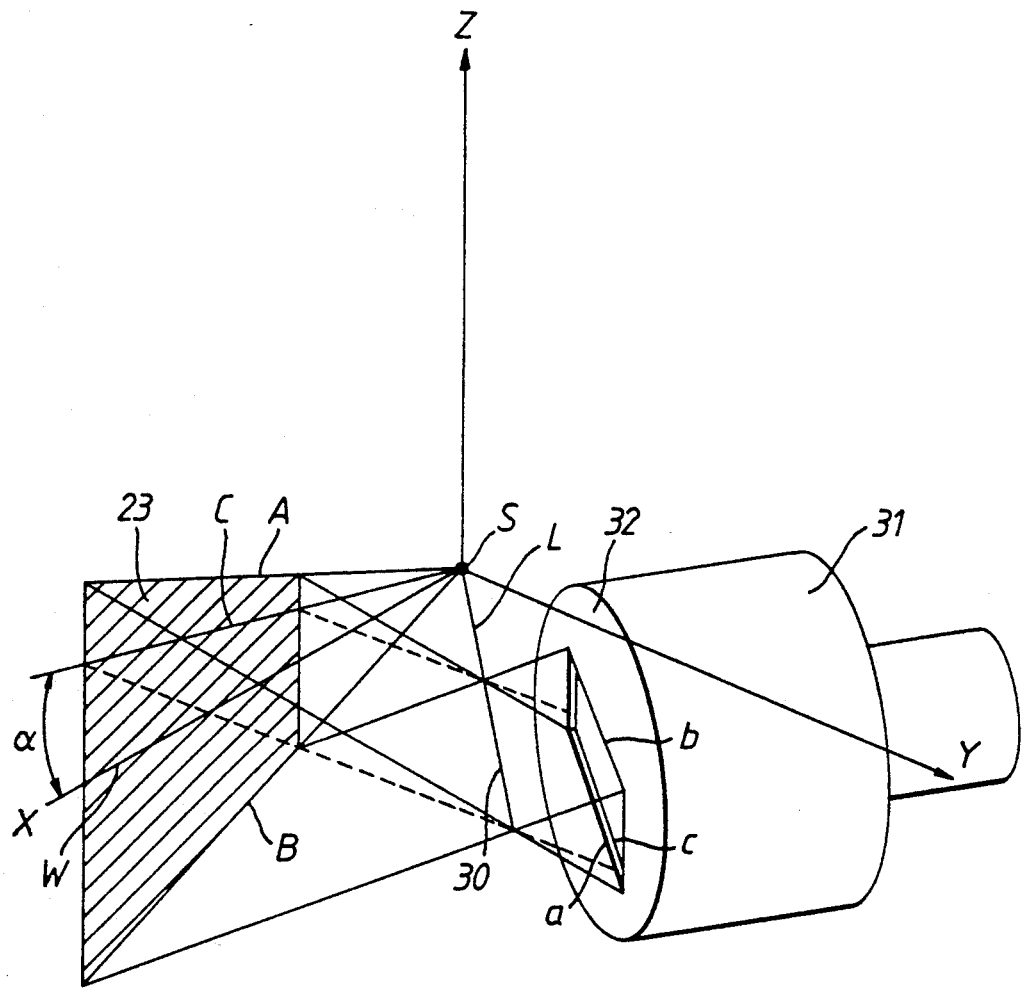
FIG. 3 is a view showing operation of a first embodiment of the present invention.
Figure 4:
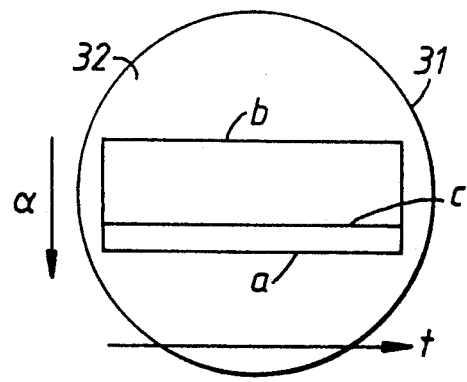
FIG. 4 is an elevational view showing a detecting face of the X-ray television of FIG. 3.

As shown in FIG. 3 and FIG. 4, the scattered X-ray beam being scattered on a line A of the fan-shaped X-ray beam is condensed on a line a on the X-ray beam detecting face 32 of the X-ray television 31. In the same way, the scattered X-ray beam being scattered on a line B is condensed on a line b on the X-ray beam detecting face 32, and the scattered X-ray beam being scattered on a line C is condensed on a line c on the X-ray beam detecting face 32.

As the X-ray beam detecting face 32 is disposed in parallel with the slit 30 formed the scattered X-ray beam pass means 29, each of the scattered X-ray beams being scattered on the lines A through C forms an image as a scattered X-ray beam image of parallel lines a through c on the detecting face 32.

The vertical direction of the scattered X-ray beam a, b, c being condensed on the detecting face 32 corresponds to the angles between the lines A through C of the fan-shaped X-ray beam and a basic line W, and the transverse direction of the scattered X-ray beam image corresponds to the transverse scanning direction of the X-ray television 31.

The way of the scanning of the X-ray television 31 is used a raster scanning for an eight-millisecond period.

The output of a twenty-microsecond period of the X-ray television 31 is integrated during the transverse scanning, and converted from an analog signal into a digital signal by the data acquisition means 37. Four hundred sets of data are acquired by the data acquisition means 37 after the conversion.

The acquired four hundred data are corrected respectively.

The method of the correction is the same as described above for the data acquisition means 35. After the correction, the corrected data is memorized in a memory (not shown) of the display device 36 as "1 line data". At this time, "1 line data" is memorized in the memory being appropriate to a vertical line of the left side of a screen (not shown) of the display device 36. The next eight-millisecond period "1 line data" is detected in the same way as described above, the next "1 line data" is memorized in the direction to the right side of the previous "1 line data" in the memory and so forth.

So whenever, the conveyor belt 25 moves two millimeters, the "1 line data" is measured. If the conveyor belt 25 moves one meter, five hundred sets of "1 line data" are measured. Accordingly a scattered X-ray beam image which is suitable for the article 26 is memorized in the memory of the display device 36, and is displayed on the screen of the display device 36.

As described above, according to this embodiment as the efficiency of measuring the scattered X-ray beam and the primary X-ray beam is improved, the quality of pictures of the scattered X-ray beam image and the primary X-ray beam image are improved.

Table 1 compares merit valves about the scattered X-ray beam image and the primary X-ray beam image of this embodiment and the prior art.

The numbers used indicate a relative value that is proportional to the number of photons of the measured scattered X-ray beam image and primary X-ray beam image. The number of photons of the measured primary X-ray beam image is defined as 1 in Table 1.

TABLE 1

|  | Scattered X-ray beam image | Primary X-ray beam image |
| --- | --- | --- |
| This embodiment | approximately 400 | approximately 400 |
| The prior art | approximately 1 | 400 |

As shown in Table 1, the number of photons of the measured scattered X-ray beam image in this embodiment is more than that in the prior art, and the number of photons of the measured primary X-ray beam image in this embodiment is approximately same as that in the prior art.

Figure 5:
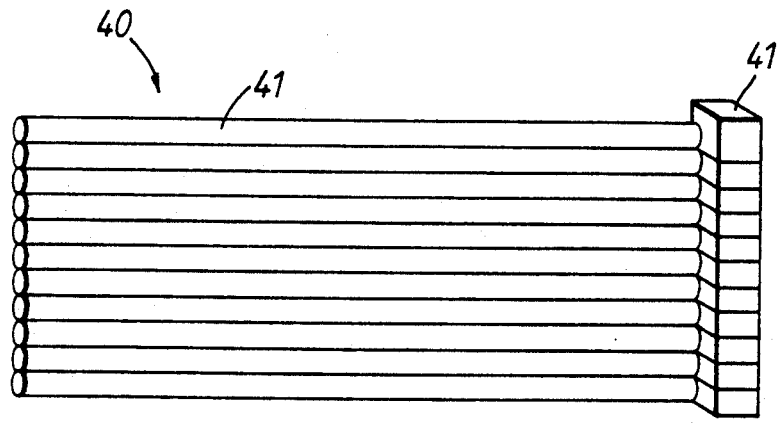
FIG. 5 is a perspective view showing a second embodiment of the radiation detector.
Figure 6:
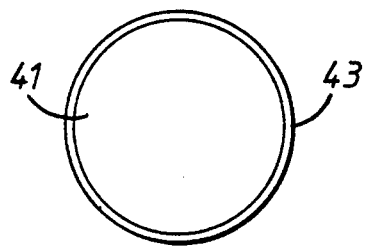
FIG. 6 is an expanded sectional view showing a line-typed scintillator of FIG. 5.
Figure 7:
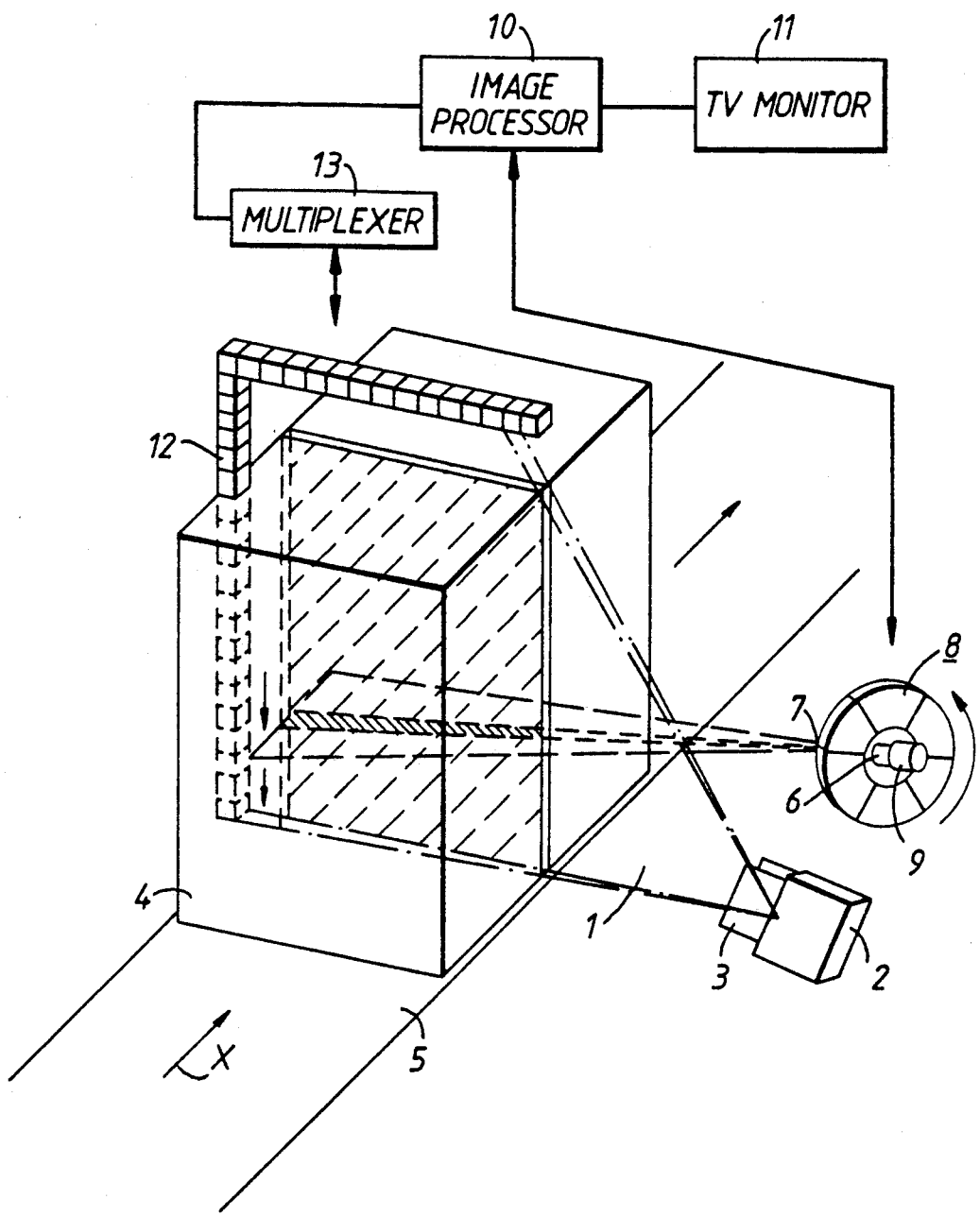
FIG. 7 is a perspective view showing a prior art example.

It should be noted that, although in the above embodiment the X-ray television 31 is used for detecting the scattered X-ray beam, as shown in FIGS. 5 and 6 for example, a line detector 40 including plural line-type scintillators 41 optically coupled with a photodiode array 42. The scintillators 41 convert scattered X-rays to visible light detected by photodiodes of the photodiode array 42. Applied to the surface of the scintillators 41 is evaporated aluminum leaf 43 to prevent intercepting of external visible rays and keeping beams generated from the inside in the scintillator 41. Besides the aluminium leaf 42, silver leaf or the silver leaf applied white coating could be used for that.

And then besides the line-typed scintillator 41, a fiber scintillator which is made of glass fiber and emits light when an X ray is irradiated may be used. The fiber scintillator is well-known. A surface of the fiber scintillator could be provided with evaporated aluminium leaf and so on in order to improve efficiency for detecting.

And also in the above embodiment the display devices 34, 36 are disposed near each other, but the scattered X-ray beam image and the primary X-ray beam image could be displayed on one display device only. Then as the scattered X-ray beam image indicates green color and the primary X-ray beam image indicates red color on the display device, the images could be easily distinguished.

Accordingly in this invention, as the slit of the pass means is located to be coincident with the line passed through the radiation and the detecting face of the radiation detect means is disposed in parallel with the slit, the radiation detect means can detect parallel scattered radiations at the same time. Also according to this invention, as a point where the primary radiation is detected corresponds to a point where the scattered radiation is detected, both of the primary image and the scattered image can be monitored on the same display.

Although the invention has been described in its preferred form with a certain degree of particularity, it is understood that the present disclosure of the preferred form may be changed in the details of construction and the combination and arrangement of parts may be changed to without departing from the spirit and the scope of the invention as hereinafter claimed.

What is claimed is:

1. A device for inspecting an article, comprising:
    radiation generating means for generating a plane-shaped X-ray radiation and irradiating the plane-shaped radiation onto an article;
    pass means having a slit formed coincident with a line passing through a focus of the radiation generating means for continuously passing a constant full field of scattered radiation scattered by the article; and
    radiation detector means having a detecting face disposed in parallel with the slit of the pass means for detecting the scattered radiation which passes through the pass means.

2. A device for inspecting an article, comprising:
    radiation generating means for generating a plane-shaped X-ray radiation and irradiating the plane-shaped radiation onto an article;
    first pass means having a slit formed coincident with a line passing through a focus of the radiation generating means for continuously passing a constant full field of scattered radiation emitted from the article as a result of being irradiated by the plane-shaped radiation;
    scattered radiation detector means having a spatial resolution and a detecting face disposed in parallel with the slit of the first pass means for detecting the scattered radiation which passed through the first pass means;
    second pass means having a slit for passing a primary radiation which is transmitted through the article for and intercepting the scattered radiation;
    primary radiation detector means for detecting the primary radiation which passes through the second pass means;
    data acquisition means for integrating an output of the scattered radiation detector means and an output of the primary radiation detector means and converting the integrated data into digital data; and
    display means for receiving and correcting the digital data from the data acquisition means, memorizing the corrected data, and displaying an image in accordance with the memorized data.

3. A device for inspecting an article, comprising:
    radiation generating means for generating a plane-shaped X-ray radiation and irradiating the plane-shaped radiation onto an article;
    first pass means having a slit formed coincident with a line passing through a focus of the radiation generating means for continuously passing a constant full field of scattered radiation emitted from the article;
    scattered radiation detector means having a detecting face disposed in parallel with the slit of the first pass means for detecting the scattered radiation which passes through the first pass means;
    second pass means having a slit for passing a primary radiation which is transmitted through the article and for intercepting the scattered radiation; and
    primary radiation detector means for detecting the primary radiation which passes through the second pass means.

4. A device for inspecting an article as claimed in claim 1 or 3, wherein the radiation generating means comprimises an X-ray tube which generates an X-ray beam and a slit which is disposed in front of the X-ray tube.

5. A device for inspecting an article as claimed in claim 1 or 3, wherein the scattered radiation detector means comprimises an X-ray television.

6. A device for inspecting an article as claimed in claim 1 or 3, wherein the scattered radiation detector means comprises:
    a line detector having a photo-diode array; and
    plural line-type scintillators coupled to the photo-diode array and having a surface which includes evaporated aluminum leaf.

7. A device for inspecting an article as claimed in claim 1 or 3, wherein the scattered radiation detector means comprises:
    a line detector having a photo-diode array; and
    plural line-type scintillators coupled to the photo-diode array and having a surface which includes evaporated silver leaf.

8. A device for inspecting an article as claimed in claim 1 or 3, wherein the scattered radiation detector means comprimises a fiber scintillator which is made of glass fiber.

* * * * *